United States Patent [19]
Davies et al.

[11] Patent Number: 5,321,970
[45] Date of Patent: Jun. 21, 1994

[54] METHOD AND APPARATUS FOR CALIBRATING A SPECTROMETER

[76] Inventors: Anthony M. C. Davies, 75 Intwood Road, Cringleford, Norwich NR4 6AA, England; Harald A. Martens, Ski Business Park, P.O. Box 1384, N-1401 Ski, Norway

[21] Appl. No.: 872,235

[22] Filed: Apr. 22, 1992

[51] Int. Cl.[5] .................. G01J 3/00; G01J 3/24
[52] U.S. Cl. ........................... 73/1 R; 356/328
[58] Field of Search .............. 73/1 R; 250/252.1 A, 250/252.1 R, 339; 356/328, 243

[56] References Cited

U.S. PATENT DOCUMENTS

| | | | |
|---|---|---|---|
| 3,518,002 | 6/1970 | Barringer et al. | 356/310 |
| 3,663,106 | 5/1972 | Minami et al. | 356/89 |
| 3,700,332 | 10/1972 | Decker, Jr. | 356/310 |
| 3,752,585 | 8/1973 | Elliott | 356/310 |
| 3,975,099 | 8/1976 | Taylor | 356/89 |
| 4,049,353 | 9/1977 | Missio | 356/310 |
| 4,084,906 | 4/1978 | Bibbero | 356/96 |
| 4,231,663 | 11/1980 | Phillippi | 335/432 |
| 4,615,619 | 10/1986 | Fateley | 356/310 |

FOREIGN PATENT DOCUMENTS

| | | |
|---|---|---|
| 0503914 | 9/1992 | European Pat. Off. ..... G01N 21/27 |
| 861206 | 2/1961 | United Kingdom . |

*Primary Examiner*—Hezron E. Williams
*Assistant Examiner*—Daniel S. Larkin
*Attorney, Agent, or Firm*—Lane, Aitken & McCann

[57] ABSTRACT

A calibration device for use in a spectrometer has a source of electromagnetic radiation, a detector for detecting electromagnetic radiation from the source, a device for recording the output of the detector, and at least one optical element in an optical path between the source and the detector to separate the electromagnetic radiation into spectral elements separately detected by the detector. The calibration device includes a variation mechanism to selectively modulate the intensity of each spectral element detected by the detector and a mechanism to adjust the variation mechanism so that the input of the detector substantially reproduces the input of electromagnetic radiation that the detector would receive in its normal operation from a sample which the spectrometer is intended to analyse.

9 Claims, 2 Drawing Sheets

METHOD AND APPARATUS FOR CALIBRATING A SPECTROMETER

FIELD OF THE INVENTION

The invention relates to a method and apparatus for calibrating spectrometers.

REVIEW OF THE ART KNOWN TO THE APPLICANTS

Spectrometers have been used for many years as analytical instruments. They rely on the characteristic reaction of many substances to incident electromagnetic radiation. Traditionally the field of spectroscopy has been divided into many different specialities. Because of the different physics, and different apparatus involved in the various types of spectroscopy, and even spectroscopy using different ranges of wavelengths, it is not surprising that such distinctions arise.

The present invention is especially concerned with the near infrared range. That range is commonly regarded as being between the wavelengths of about 750 nm to about 2500 nm. Near infrared spectrometry is a technique which is widely used for the quantitative analysis of natural and synthetic organic samples, especially agricultural commodities.

Conventional dispersive infrared spectrometers operate in the following manner. Infrared radiation is emitted from a black-body radiation source, is divided into spectral elements by a dispersion grating or filter, collected by a mirror, and focused onto a sample. The infrared radiation either transmitted or reflected by the sample is registered on a detector. A spectral element is typically understood, in this field, to be a relatively narrow band of radiation comprising a small interval of the relevant wavelength spectrum.

A range of spectral elements can be focused onto the sample so that the detector can build up a spectrum of the transmission or reflection properties of the sample over the full near infrared spectrum. The spectrometer will, generally, compare the properties of the beam that has been incident on the sample with a reference beam. The reference beam may, for instance, be that resulting from the original beam being incident on a ceramic, or other, standard.

Typically the results of such an analysis are presented graphically with a range of wavelengths along one axis and, if the reflection (R) of the sample is being measured, $\log_{10}(1/R)$ along the other axis. This information can then be assessed, normally by computer, in order to determine the composition of the sample.

As the measurements are compared with previous samples, the spectrometers must be calibrated. This has typically been done by analysing a large number (normally 50 or more) of samples with known constituents.

Despite the best efforts of the manufacturers, it is accepted that supposedly identical spectrometers will differ from each other in significant ways. More particularly, the items in the optical path of the spectrometer are found to have differing transmission and/or reflection properties when comparing one spectrometer with another. This is especially so in the case of the detectors in the spectrometers. To achieve even the present levels of accuracy, complex cooling devices have had to be used in conjunction with the spectrometers to reduce the noise levels.

The result of this is that if a spectrogram is produced for a given sample on a first (master) spectrometer, and then the sample is transferred to a second (slave) spectrometer which produces a spectrum, the two spectrums may differ significantly. Thus, a standard set of spectrums produced on one machine may not necessarily be accurately transferable to other spectrometers. This has led to inherent inaccuracies in measuring the amounts of various materials in some samples. Therefore the main difficulty is in accurately transferring calibrations between spectrometers.

Before analysing a sample it is frequently necessary to check the calibration of the spectrometer that is being used. This is performed by analysing known samples and measuring the error between the empirical and known values for the samples. A skew, or bias, can be introduced into the data handling routines of the data analysis equipment of the spectrometer to compensate for these differences.

More particularly there is a problem with new samples. If one laboratory analyses the near infrared spectrum of a sample, it is advantageous if it can inform other laboratories of the results in order to assist in their analysis. However, as discussed above, the other laboratories' machines may not produce the same spectrum from the sample due to differences in the machines and the samples.

U.S. Pat. No. 4,615,619 (Fateley) discloses a stationary, electrically alterable, optical masking device and a spectroscopic apparatus employing this masking device. The apparatus disclosed includes a source of electromagnetic radiation, a slit plate, a grating, an alterable mask, a lens and a detector. A computer is used to monitor the detector and to control the electrically alterable mask. The mask can be rapidly altered by this electrical control and is used to enable Hadamard Transform Spectroscopy to be carried out. This is a dispersive technique which also enjoys some of the advantages of Fourier Transform Spectroscopy. There is no suggestion in this specification that the alterable mask could be used to calibrate a spectrometer.

Thus there is a genuine need for a means of calibrating spectrometers that is transferable between machines, accurate, time-efficient and preferably non-labour intensive.

SUMMARY OF THE INVENTION

According to the invention in its broadest aspect, there is provided a calibration means suitable for, and intended for use in a spectrometer comprising a source of electromagnetic radiation, a detector suitable for detecting electromagnetic radiation from the source, recording means for recording the output of the detector and at least one optical element in the optical path between the source and the detector, the calibration means comprising a variation means to enable the input of electromagnetic radiation to the detector to be varied and an adjustment means to adjust the variation means adapted so that the input of the detector substantially reproduces the input of electromagnetic radiation that the detector would receive in its normal operation from a sample which the spectrometer is intended to analyse.

Conveniently the variation means comprises an electrodiachromatic mask which is located in the optical path of the spectrometer and which is capable of modulating the transmission of the electromagnetic radiation from the source by adjusting the optical density of the mask. The adjustment means may comprise an electrical control means which is capable of adjusting the optical density of the electrodiachromatic mask.

Typically the detector is used to detect a spectral element within a desired range of wavelengths to be detected and the detector measures a plurality of spectral elements in the desired wavelength range to build up a complete spectrum. In this case the variation means is normally adjusted by the adjustment means between the measurement by the detector of each spectral element.

The invention also encompasses a spectrometer including a calibration means of the type described above.

Optionally the spectrometer may be intended for, and capable of use with electromagnetic radiation having a wavelength in the range from about 750 nm to about 2500 nm.

The spectrometer may conveniently be a dispersive spectrometer. In this case one of the optical elements may comprise a dispersion means.

Advantageously the recording means records the output from the detector in digital form. Furthermore the spectrometer may include storage means to store data to control the adjustment means.

Also within the broadest ambit of the invention is a storage means which stores data suitable for use in controlling the adjustment means in the apparatus described above.

The present invention additionally provides a method of calibrating a spectrometer which comprises a source of electromagnetic radiation, a detector suitable for detecting electromagnetic radiation from the source, at least one optical element in the optical path between the source and the detector, a recording means, and a calibration means which comprises a variation means and an adjustment means, which method includes the steps of:

(a) selecting a material to be analysed,
(b) positioning the variation means to enable the input of electromagnetic radiation to the detector to be varied,
(c) operating the adjustment means to adjust the variation means to substantially reproduce the input of electromagnetic radiation that the detector would receive in its normal operation from the sample which the spectrometer is intended to anlayse, and
(d) recording the output of the detector using the recording means.

In the method described above, advantageously an electrodiachromatic mask is chosen as the variation means and is positioned in the optical path of the spectrometer.

DESCRIPTION OF THE PREFERRED EMBODIMENTS

The invention will now be described, by way of example only, with reference to the following drawings. The preferred embodiment described below is based on a dispersive near infrared spectrometer. However, the invention is not limited to this type of spectrometer and extends to non-dispersive spectrometers (e.g. Filter Instruments, Fourier Transform Spectrometers). The invention is also applicable to spectrometers working outside, in part or in whole, the near infrared range. The invention may be especially usefully employed in a spectrometer utilising wavelengths between about 750 nm and about 1200 nm and between about 400 nm and about 2500 nm, amongst others.

Figure 1:
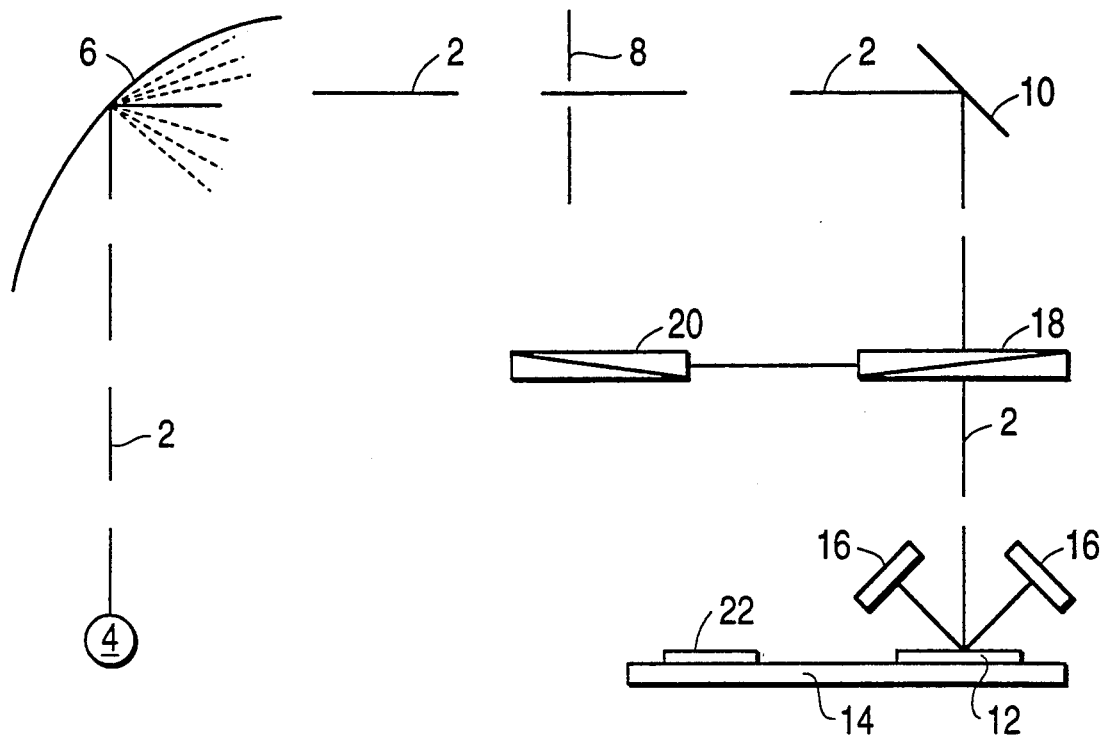
FIG. 1 is a schematic diagram depicting one currently preferred embodiment of a spectrometer including the present invention.

Referring now to FIG. 1 of the drawings. A beam of radiation 2 is shown being emitted from a source of electromagnetic radiation 4. The source 4 emits radiation in the range of from about 1100 nm to about 2500 nm, over which range the intensity of the emitted radiation is known and substantially constant over time. It should be noted that in some cases the sample itself may be the source of electromagnetic radiation, such as in the area of spectroradiometry.

Following the beam of radiation 2 from the source 4, its first impinges on a dispersion means 6 which comprises a known dispersion grating which is capable of being rotated. The dispersion means 6 disperse the incoming radiation to an angle relative to the incoming beam that is dependent on the wavelength of the dispersed radiation. Some of the dispersed beams are shown in FIG. 1.

Following the beam of radiation 2, it then passes through a slit 8. The slit allows only those wavelengths of the radiation that have been dispersed at certain angles to pass therethrough. Thus, the beam of radiation 2 which passes through the slit 8 comprises a bundle of wavelengths, i.e. a spectral element. As the dispersion means 6 is rotated the spectral elements that pass through the slit 8 are varied in a controllable fashion. The well established laws of optics allow the wavelengths that pass through the slit to be determined.

The beam of radiation 2 is next reflected off an infrared mirror 10 towards the sample 12 which is shown on a staging plate 14. In this case, the beam 2 is then reflected off the sample 12 with the intensity of the reflected beam 2 being measured by detectors 16.

Between the infrared mirror 10 and the sample 12, the beam of radiation passes through a variation means 18. The variation means has the ability to adjust its optical density in a controllable manner, and is more fully discussed below. In order to control the optical density of the variation means an adjustment means 20 is provided; this is also discussed more fully below. The variation means 18 and the adjustment means 20 together constitute the calibration means.

The spectrometer may include other optical elements, for instance a focusing device. However for the sake of simplicity, and to facilitate the explanation of the invention, these other optical elements are not shown.

Also shown on the staging plate 14 is a ceramic standard 22 which has known infrared reflecting properties. In conventional spectrometers this is used to produce the reference against which the beam incident on the sample is compared. In the embodiment shown in the figures a complete spectrum is taken using the ceramic standard and then the sample is analysed using this spectrum as a reference.

Figure 2:
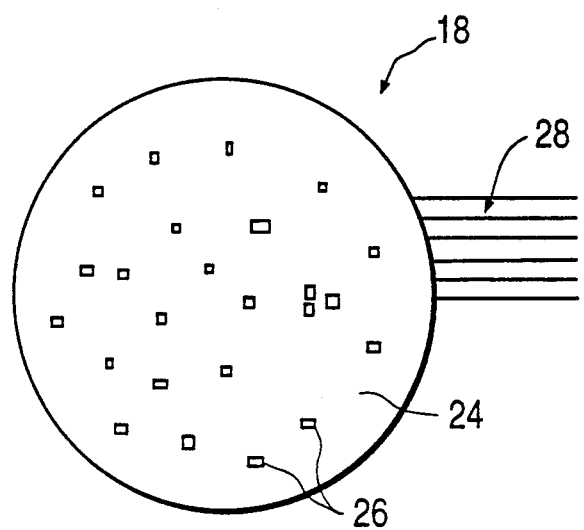
FIG. 2 illustrates the variation means shown in the FIG. 1.

Referring now, additionally, to FIG. 2 of the drawings. The variation means 18 comprises an electrodiachromatic mask, which in this case is a liquid crystal display (LCD) 24. The LCD 24 may be of any shape, although in this case only a substantially circular part of the mask having a diameter of approximately 2 cm is required. The relevant circular area of the mask contains 500 substantially bistable cells 26 which can be in either a transmitting or a darkened state for infrared radiation. The changes in the LCD may vary the intensity and/or the wavelength distributed and/or the angular distribution of the transmitted radiation. Each of these effects, alone or in combination may be used to modulate the intensity of the radiation incident on the detectors. Thus the LCD can be a multi-colour LCD. The LCD used preferably has a low hysteresis. Some of the darkened cells are shown in FIG. 2. Although an LCD is currently the preferred variation means other variation means may be used. It may even be possible to use a simple mechanical shutter as the variation means.

Also shown in the FIG. 2 are a few of the wires 28 which lead to the adjustment means 20 which is used to control the optical density of the LCD 24. The adjustment means will generally comprise a computer controlled multiplexing system.

It is essential that the adjustment means is capable of controlling the variation means so that the input of the detector of the spectrometer is substantially a reproduction of the input of electromagnetic radiation that the detector would receive in its normal operation from a sample which the spectrometer is intended to analyse.

Figure 3:
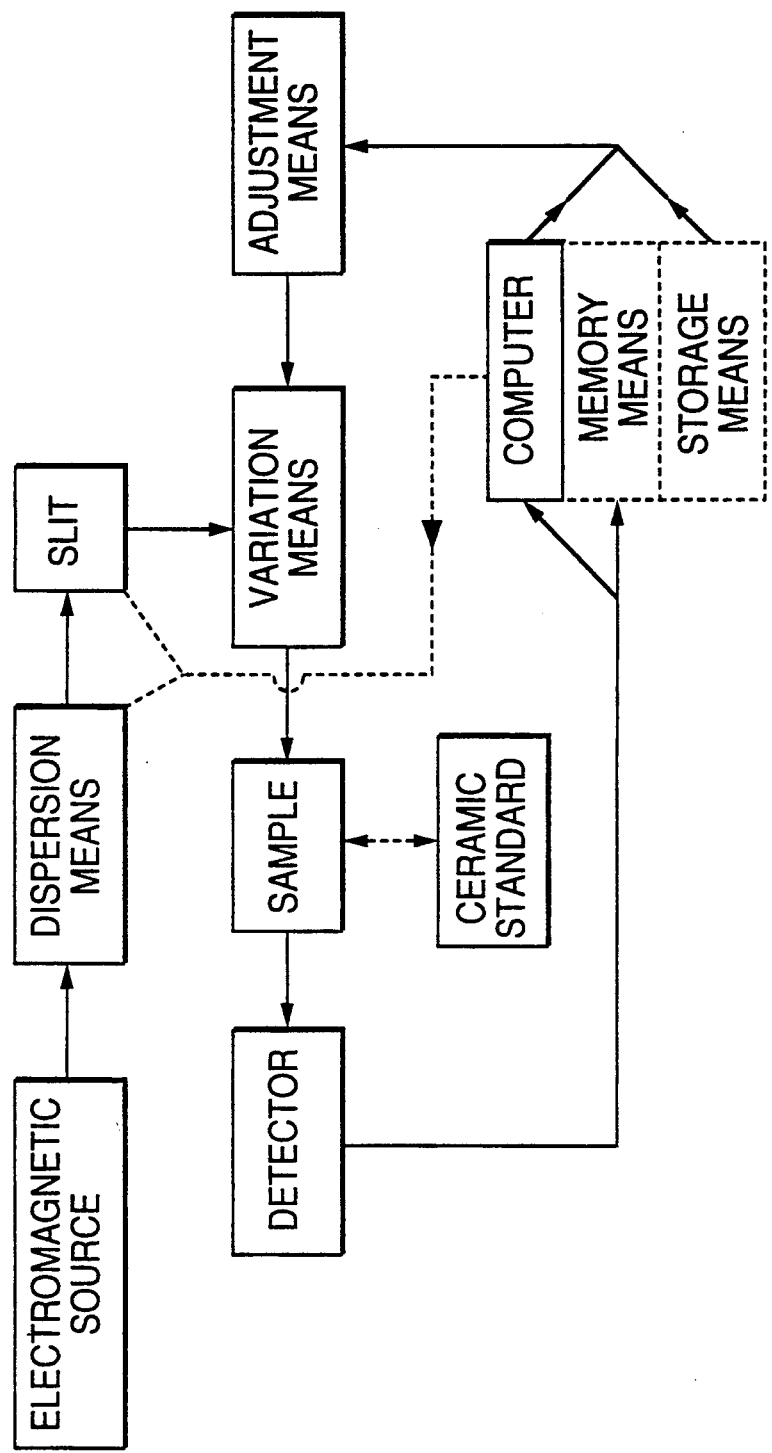
FIG. 3 is a block diagram illustrating the method of operation of the present invention.

The mode of operation of the invention will now be described with special reference to FIG. 3 of the drawings. As discussed above, the beam of radiation emitted by the source is broken down and limited to spectral elements by the action of the dispersion means and the beam restricting means (the slit 8 above). The spectral element then passes through the variation means and is incident on the sample. A proportion of the reflected radiation is received by the detectors.

In the preferred embodiment the spectral element comprises a packet of wavelengths having a bandwidth of about 10 nm. The spectrometer takes readings at 2 nm intervals. The detector therefore needs to take about 700 readings in order to build up a full spectrogram across the range of wavelengths from 1100 nm to 2500 nm which is typical wavelength range used in practice. The detector measures a plurality of spectral elements in the desired wavelength range to build up a complete spectrum.

The adjustment means comprises an electrical control means which is managed by a computer system. The computer may also perform the function of a recording means to record the output from the detector in digital form and the function of a storage means to store data to control the adjustment means. Although, for convenience, this is described as a single computer, in reality it is likely to be necessary to use several computers to perform these functions, depending on the computing "power" available. The electrical control means can be produced from known components.

The calibration of the spectrometer is performed as follows. A material is selected which it is desired to analyse. The ceramic standard is inserted in place of the sample. The source of electromagnetic radiation is energized and the dispersion means is adjusted, in combination with the slit, to allow a first spectral element of determined bandwidth (e.g. 10 nm) to pass through the slit. The intensity of the radiation in the first spectral element that would be reflected by the sample which the spectrometer is intended to analyse is known. This information is stored in the computer and used to instruct the adjustment means to adjust the liquid crystal displays optical density to match the intensity that would be reflected by the sample were it in place. The adjustment means is then instructed by the computer to adjust the optical density of the variation means. This adjustment occurs in accordance with the instructions held by the computer in the storage means. The adjustment means adjusts the optical density of the variation means to substantially reproduce the input of electromagnetic radiation that the detector would receive in its normal operation from the sample which the spectrometer is intended to analyse.

In this way, the spectrometer is effectively fooled into 'thinking' that the sample is in place. The present invention thus removes the necessity for such samples to be used.

Depending on the method used the dispersion means may be adjusted to enable a further 10 nm band pass or further measurements may be taken in the 10 nm bandwidth before the dispersion means is adjusted. In either case, after the measurement(s) is(are) made, the dispersion means is then adjusted, in this case the dispersion grating is rotated, to enable the next spectral element to pass through the slit. During this time the adjustment means may adjust the optical density of the variation means in accordance with the instructions from the computer system. Alternatively, if several measurements are made within a band pass the optical density of the variation means may be varied between each measurement as well. The present inventors have determined that, in order to obtain satisfactory results, the optical density of the adjustment means must be varied to within $10^{-4}$ units of optical density.

Thus the spectrometer cycles through each spectral element until a complete spectrum is built up.

When the calibration means is used on any machine, it is likely that the spectrum it produces will not be exactly that required because of the interruption of the calibration means with the spectrometer, and the fact that the variation means has a non-zero optical density even in its most transmitting state. This latter cause may introduce a systematic error into the readings. The computer controlling the operation and monitoring of the spectrometer can vary the instructions to the adjustment means, which controls the optical density of the variation means, to compensate for these errors, as much as possible.

The original data used to control the adjustment means in the method described above can be obtained from several sources. For instance, any suitable near infrared spectrometer can be used to obtain an original spectrum of a known material or some other well defined signal generation pattern, generating 'reference spectra'. Spectra for a set of such materials or patterns can thus be established to represent 'reference instrument' A. Using the present invention instead of real samples in a new instrument B, corresponding measured spectra can be obtained in instrument B, but differing from A's spectra because of systematic instrument differences.

Multivariate statistical modelling, (bilinear modelling like PLSR and nonlinear versions of these, neural nets etc) can then be used for establishing mathematical transfer functions between data from instruments A and B. These transfer functions can then be used for modifying future spectra of real samples in instrument B, or for modifying previously established calibration models from instrument A or instrument B, depending on how the transfer functions are defined.

If a spectrometer is then calibrated using the data from this machine then the two spectrometers will be calibrated with respect to one another for that given sample. There is even the possibility that the data could be artificially produced for some special purposes. For instance, artificially produced data could be useful for defining an underlying parameter space, e.g. a "Principal Component Space" within which spectra can be measured, as will be appreciated by those skilled in the art.

The LCD that comprises the variation means in the embodiment described above can equally well be used in other positions in the optical path. At an extreme the LCD can be located on the staging plate in place of the sample. Although in this case it can be used to limit the transmission of the radiation therethrough, it is more convenient to use it to limit the reflection of radiation to the detectors. Another alternative is to use an array of light-emitting diodes which transmit electromagnetic radiation at the frequencies to which the detector is sensitive and which can be adjusted to enable the intensity of radiation entering the detectors to be controllably varied.

It should be noted that optically tuned filters could be used in place of the LCD or even the dispersion means. These filters produce two equal, divergent beams of radiation from an incident beam; the wavelengths of the divergent beams are dependent on the frequency of an audio signal which is also incident on the filter and which is electrically controlled by the computer.

It is perceived that the present invention will be useful in both the retro-fit and the original manufacturing markets. For the retro-fit market the embodiment of the present invention wherein the variation means is located on the staging plate in place of the sample is to be preferred. If the present invention is to be incorporated in a spectrometer permanently, then it is preferable that the variation means is located within the body of the spectrometer; the position schematically illustrated in FIG. 1 would, normally, be suitable. In this latter application the variation means would simply remain in its transmitting state whilst the spectrometer was in normal use, or it could be rotated out of the optical path.

The present invention thus provides an apparatus and method for calibrating a spectrometer which can be automatic, versatile and efficient. The invention allows spectrometers to be calibrated with respect to each other, and to agreed standards. By utilising the present invention there would be no need, for instance, for new organic samples to be distributed around laboratories so that each one could establish a calibration spectrum; with the associated difficulties involved with transporting such a sample. Using the present invention one laboratory can analyse such organic samples and produce definitive spectra which can be communicated in digital form (e.g. on a floppy disk, or even along the phone lines) for others to calibrate their instruments to match the original spectrometer.

To summarise, there are two main advantages in using the present invention. One is that it can be used to replace the set of samples which would normally be required to correct a 'slave' instrument, according to the present mode of operation. Another main advantage is that it can be used in techniques utilising underlying parameter spaces, such as Principal Component Analysis, again as a replacement for standard samples without the need for those samples to be transferred from one laboratory to another. Another use to which the present invention could be extended, is in real-time corrections. This technique could be used to reduce the effects of the differences between 'master' and 'slave' spectrometers. The reference spectra of a 'slave' spectrometer could be equated to reference spectra from a 'master' spectrometer using the present invention. These adjustments could then be included in a real-time measurement of a sample the 'slave' spectrometer would then, in theory, behave in an equivalent manner to the 'master' spectrometer.

We claim:

1. A calibration means suitable for, and intended for use in a spectrometer comprising a source of electromagnetic radiation, a detector suitable for detecting electromagnetic radiation from the source, recording means for recording the output of the detector and at least one optical element in the optical path between the source and the detector to separate said electromagnetic radiation into spectral elements separately detected by said detector, the calibration means comprising a variation means to selectively modulate the intensity of each spectral element detected by the detector and an adjustment means to adjust the variation means adapted so that the input of the detector substantially reproduces the input of electromagnetic radiation that the detector would receive in its normal operation from a sample which the spectrometer is intended to analyse.

2. A calibration means according to claim 1 in which the variation means comprises a liquid crystal display which is located in the optical path of the spectrometer and which is capable of modulating the transmission of the electromagnetic radiation from the source by adjusting the optical density of the mask.

3. A calibration means according to claim 2 in which the adjustment means comprises an electrical control means which is capable of adjusting the optical density of the liquid crystal display.

4. A calibration means according to claim 1 in which the spectrometer is intended for, and capable of use with electromagnetic radiation having a wavelength in the range from about 750 nm to about 2500 nm.

5. A calibration means according to claim 4 in which the spectrometer is a dispersive spectrometer wherein said optical element disperses said electromagnetic radiation into spectral elements.

6. A calibration means according to claim 5 in which a recording means records the output from the detector in digital form.

7. A calibration means according to claim 1 in which a storage means stores data suitable for use in controlling the adjustment means.

8. A method of calibrating a spectrometer which comprises a source of electromagnetic radiation, a detector suitable for detecting electromagnetic radiation from the source, at least one optical element in the optical path between the source and the detector to separate said electromagnetic radiation into spectral elements, a recording means, and a calibration means which comprises a variation means and an adjustment means which method includes the steps of:
   a) selecting a material to be analysed,
   b) positioning the variation means to enable the input of each spectral element of electromagnetic radiation to the detector to be varied,
   c) operating the adjustment means to adjust the variation means to substantially reproduce the input of each spectral element of electromagnetic radiation that the detector would receive in its normal operation from the sample which the spectrometer is intended to analyse, and
   d) recording the output of the detector using the recording means.

9. A method of calibrating a spectrometer according to claim number 8 in which a liquid crystal display is the variation means and is positioned in the optical path of the spectrometer.

* * * * *